United States Patent
Kaplan et al.

(10) Patent No.: US 7,717,953 B2
(45) Date of Patent: May 18, 2010

(54) DELIVERY SYSTEM FOR PLACEMENT OF PROSTHESIS AT LUMINAL OS

(75) Inventors: Aaron V. Kaplan, Norwich, VT (US); Jaime Vargas, Redwood City, CA (US)

(73) Assignee: Tryton Medical, Inc., Durham, NC (US)

( * ) Notice: Subject to any disclaimer, the term of this patent is extended or adjusted under 35 U.S.C. 154(b) by 317 days.

(21) Appl. No.: 10/965,230

(22) Filed: Oct. 13, 2004

(65) Prior Publication Data

US 2006/0079952 A1    Apr. 13, 2006

(51) Int. Cl.
*A61F 2/06* (2006.01)
(52) U.S. Cl. .................. 623/1.35; 623/1.12
(58) Field of Classification Search ........... 623/1.11, 623/1.12, 1.35
See application file for complete search history.

(56) References Cited

U.S. PATENT DOCUMENTS

| | | | |
|---|---|---|---|
| 4,950,227 A * | 8/1990 | Savin et al. ............. | 623/1.12 |
| 4,958,634 A | 9/1990 | Jang | |
| 4,994,071 A | 2/1991 | MacGregor | |
| 5,071,406 A | 12/1991 | Jang | |
| 5,074,845 A | 12/1991 | Miraki et al. | |
| 5,102,417 A | 4/1992 | Palmaz | |
| 5,226,889 A | 7/1993 | Sheiban | |
| 5,304,132 A | 4/1994 | Jang | |
| 5,342,387 A | 8/1994 | Summers | |
| 5,383,892 A | 1/1995 | Cardon et al. | |
| 5,395,333 A | 3/1995 | Brill | |
| 5,415,635 A | 5/1995 | Bagaoisan et al. | |
| 5,507,769 A | 4/1996 | Marin et al. | |
| 5,522,882 A | 6/1996 | Gaterud et al. | |
| 5,540,712 A | 7/1996 | Kleshinski et al. | |
| 5,575,817 A | 11/1996 | Martin | |
| 5,593,442 A | 1/1997 | Klein | |
| 5,607,444 A | 3/1997 | Lam | |
| 5,609,605 A | 3/1997 | Marshall et al. | |
| 5,609,627 A | 3/1997 | Goicoechea et al. | |

(Continued)

FOREIGN PATENT DOCUMENTS

EP    0712614 B1    5/1996

(Continued)

OTHER PUBLICATIONS

Baldus et al., "Protection of Side-Branches in Coronary Lesions with a New Stent Design", *Cathet Cardiovasc Diagn*, (Dec. 1998), 45(4):456-459.

(Continued)

*Primary Examiner*—Todd E Manahan
*Assistant Examiner*—Katherine M Dowe
(74) *Attorney, Agent, or Firm*—Knobbe, Martens, Olson & Bear, LLP

(57) ABSTRACT

An embodiment of the invention provides a prosthesis delivery system comprising a delivery catheter having an expandable member and a prosthesis carried over the expandable member. The prosthesis includes a radially expandable scaffold section and at least two anchors extending axially from an end thereof; and means for capturing at least the anchors to prevent the anchors from divaricating from the expandable member as the catheter is advanced through a patient's vasculature.

24 Claims, 9 Drawing Sheets

U.S. PATENT DOCUMENTS

| | | | |
|---|---|---|---|
| 5,613,980 A | 3/1997 | Chauhan | |
| 5,628,783 A * | 5/1997 | Quiachon et al. | 623/1.35 |
| 5,632,762 A | 5/1997 | Myler | |
| 5,632,772 A | 5/1997 | Alcime et al. | |
| 5,645,560 A | 7/1997 | Crocker et al. | |
| 5,656,036 A | 8/1997 | Palmaz | |
| 5,658,251 A | 8/1997 | Ressemann et al. | |
| 5,662,608 A | 9/1997 | Imran et al. | |
| 5,669,924 A | 9/1997 | Shaknovich | |
| 5,669,932 A | 9/1997 | Fischell et al. | |
| 5,713,917 A | 2/1998 | Leonhardt et al. | |
| 5,718,712 A | 2/1998 | Bonnai et al. | |
| 5,720,724 A | 2/1998 | Ressemann et al. | |
| 5,720,735 A | 2/1998 | Dorros | |
| 5,741,325 A | 4/1998 | Chaikof et al. | |
| 5,749,825 A | 5/1998 | Fischell et al. | |
| 5,749,851 A | 5/1998 | Wang | |
| 5,749,890 A | 5/1998 | Shaknovich | |
| 5,755,734 A | 5/1998 | Richter et al. | |
| 5,755,735 A | 5/1998 | Richter et al. | |
| 5,755,771 A | 5/1998 | Penn et al. | |
| 5,755,781 A | 5/1998 | Jayaraman | |
| 5,788,708 A | 8/1998 | Hegde et al. | |
| 5,810,871 A | 9/1998 | Tuckey et al. | |
| 5,824,052 A * | 10/1998 | Khosravi et al. | 623/1.15 |
| 5,827,320 A | 10/1998 | Richter et al. | |
| 5,843,116 A | 12/1998 | Crocker et al. | |
| 5,855,598 A | 1/1999 | Pinchuk | |
| 5,860,998 A | 1/1999 | Robinson et al. | |
| 5,868,777 A | 2/1999 | Lam | |
| 5,868,783 A | 2/1999 | Tower | |
| 5,891,191 A | 4/1999 | Stinson | |
| 5,893,887 A | 4/1999 | Jayaraman | |
| 5,897,588 A | 4/1999 | Hull et al. | |
| 5,906,640 A | 5/1999 | Penn et al. | |
| 5,906,641 A | 5/1999 | Thompson et al. | |
| 5,922,019 A | 7/1999 | Hankh et al. | |
| 5,961,546 A | 10/1999 | Robinson et al. | |
| 5,964,771 A | 10/1999 | Beyar et al. | |
| 5,967,971 A | 10/1999 | Bolser | |
| 5,968,089 A * | 10/1999 | Krajicek | 623/1.15 |
| 5,980,532 A | 11/1999 | Wang | |
| 6,004,347 A | 12/1999 | McNamara et al. | |
| 6,017,363 A | 1/2000 | Hojeibane | |
| 6,027,486 A | 2/2000 | Crocker et al. | |
| 6,027,517 A | 2/2000 | Crocker et al. | |
| 6,033,434 A | 3/2000 | Borghi | |
| 6,033,435 A | 3/2000 | Penn et al. | |
| 6,048,361 A | 4/2000 | Von Oepen | |
| 6,051,020 A | 4/2000 | Goicoechea et al. | |
| 6,053,913 A | 4/2000 | Tu et al. | |
| 6,053,941 A | 4/2000 | Lindenberg et al. | |
| 6,056,775 A | 5/2000 | Borghi et al. | |
| 6,056,776 A | 5/2000 | Lau et al. | |
| 6,066,155 A | 5/2000 | Amann et al. | |
| 6,066,168 A | 5/2000 | Lau et al. | |
| 6,068,654 A * | 5/2000 | Berg et al. | 623/23.64 |
| 6,068,655 A * | 5/2000 | Seguin et al. | 623/1.35 |
| 6,077,297 A | 6/2000 | Robinson et al. | |
| 6,090,127 A | 7/2000 | Globerman | |
| 6,090,133 A | 7/2000 | Richter et al. | |
| 6,096,071 A | 8/2000 | Yadav | |
| 6,096,073 A | 8/2000 | Webster et al. | |
| 6,099,497 A | 8/2000 | Adams et al. | |
| 6,099,560 A | 8/2000 | Penn et al. | |
| 6,113,607 A | 9/2000 | Lau et al. | |
| 6,120,523 A | 9/2000 | Crocker et al. | |
| 6,127,597 A | 10/2000 | Beyar et al. | |
| 6,129,738 A | 10/2000 | Lashinski et al. | |
| 6,156,052 A | 12/2000 | Richter et al. | |
| 6,159,238 A | 12/2000 | Killion et al. | |
| 6,162,243 A | 12/2000 | Gray et al. | |
| 6,165,195 A | 12/2000 | Wilson et al. | |
| 6,168,617 B1 | 1/2001 | Blaeser et al. | |
| 6,183,509 B1 | 2/2001 | Dibi | |
| 6,206,910 B1 | 3/2001 | Berry et al. | |
| 6,210,429 B1 | 4/2001 | Vardi et al. | |
| 6,214,036 B1 | 4/2001 | Letendre et al. | |
| 6,221,080 B1 | 4/2001 | Power | |
| 6,221,096 B1 | 4/2001 | Aiba et al. | |
| 6,221,098 B1 | 4/2001 | Wilson et al. | |
| 6,231,543 B1 | 5/2001 | Hegde et al. | |
| 6,241,738 B1 | 6/2001 | Dereume | |
| 6,241,744 B1 | 6/2001 | Imran et al. | |
| 6,254,593 B1 | 7/2001 | Wilson | |
| 6,258,116 B1 | 7/2001 | Hojeibane | |
| 6,261,305 B1 | 7/2001 | Marotta et al. | |
| 6,261,316 B1 | 7/2001 | Shaolian et al. | |
| 6,264,682 B1 | 7/2001 | Wilson et al. | |
| 6,264,686 B1 | 7/2001 | Rieu et al. | |
| 6,267,783 B1 | 7/2001 | Letendre et al. | |
| 6,270,525 B1 | 8/2001 | Letendre et al. | |
| 6,280,412 B1 | 8/2001 | Pederson, Jr. et al. | |
| 6,287,315 B1 | 9/2001 | Wijeratne et al. | |
| 6,287,336 B1 | 9/2001 | Globerman et al. | |
| 6,290,728 B1 | 9/2001 | Phelps et al. | |
| 6,293,964 B1 | 9/2001 | Yadav | |
| 6,325,826 B1 * | 12/2001 | Vardi et al. | 623/1.35 |
| 6,331,186 B1 | 12/2001 | Wang et al. | |
| 6,344,052 B1 | 2/2002 | Greenan et al. | |
| 6,346,089 B1 | 2/2002 | Dibie | |
| 6,352,551 B1 | 3/2002 | Wang | |
| 6,361,544 B1 | 3/2002 | Wilson et al. | |
| 6,383,212 B2 | 5/2002 | Durcan et al. | |
| 6,383,213 B2 | 5/2002 | Wilson et al. | |
| 6,387,120 B2 | 5/2002 | Wilson et al. | |
| 6,391,032 B2 | 5/2002 | Blaeser et al. | |
| 6,395,008 B1 | 5/2002 | Ellis et al. | |
| 6,402,778 B2 | 6/2002 | Wang | |
| 6,409,741 B1 | 6/2002 | Crocker et al. | |
| 6,409,750 B1 | 6/2002 | Hyodoh et al. | |
| 6,409,755 B1 | 6/2002 | Vrba | |
| 6,409,757 B1 | 6/2002 | Trout, III et al. | |
| 6,428,567 B2 | 8/2002 | Wilson et al. | |
| 6,436,104 B2 | 8/2002 | Hojeibane | |
| 6,436,134 B2 | 8/2002 | Richter et al. | |
| 6,440,165 B1 | 8/2002 | Richter et al. | |
| 6,451,050 B1 | 9/2002 | Rudakov et al. | |
| 6,478,814 B2 | 11/2002 | Wang et al. | |
| 6,482,211 B1 | 11/2002 | Choi | |
| 6,482,227 B1 | 11/2002 | Solovay | |
| 6,485,509 B2 | 11/2002 | Killion et al. | |
| 6,488,700 B2 * | 12/2002 | Klumb et al. | 623/1.12 |
| 6,508,836 B2 | 1/2003 | Wilson et al. | |
| 6,517,558 B2 | 2/2003 | Gittings et al. | |
| 6,524,335 B1 | 2/2003 | Hartley et al. | |
| 6,540,779 B2 | 4/2003 | Richter et al. | |
| 6,547,813 B2 | 4/2003 | Stiger et al. | |
| 6,554,856 B1 | 4/2003 | Doorly et al. | |
| 6,562,061 B1 | 5/2003 | Wang et al. | |
| 6,565,597 B1 | 5/2003 | Fearnot et al. | |
| 6,572,649 B2 | 6/2003 | Berry et al. | |
| 6,579,312 B2 | 6/2003 | Wilson et al. | |
| 6,579,314 B1 | 6/2003 | Lombardi et al. | |
| 6,582,394 B1 | 6/2003 | Reiss et al. | |
| 6,589,274 B2 | 7/2003 | Stiger et al. | |
| 6,596,020 B2 | 7/2003 | Vardi et al. | |
| 6,599,316 B2 | 7/2003 | Vardi et al. | |
| 6,607,552 B1 | 8/2003 | Hanson | |
| 6,626,934 B2 | 9/2003 | Blaeser et al. | |
| 6,637,107 B2 | 10/2003 | Yasuhara et al. | |
| 6,652,580 B1 | 11/2003 | Chuter et al. | |
| 6,656,215 B1 | 12/2003 | Yanez et al. | |
| 6,656,216 B1 | 12/2003 | Hossainy et al. | |

| | | | |
|---|---|---|---|
| 6,663,665 B2 | 12/2003 | Shaolian et al. | |
| 6,663,666 B1 | 12/2003 | Quiachon et al. | |
| 6,673,104 B2 | 1/2004 | Barry | |
| 6,673,106 B2 | 1/2004 | Mitelberg et al. | |
| 6,673,107 B1 | 1/2004 | Brandt et al. | |
| 6,682,557 B1 | 1/2004 | Quiachon et al. | |
| 6,706,062 B2 | 3/2004 | Vardi et al. | |
| 6,726,714 B2 | 4/2004 | DiCaprio et al. | |
| 6,740,113 B2 | 5/2004 | Vrba | |
| 6,756,094 B1 | 6/2004 | Wang et al. | |
| 6,764,504 B2 | 7/2004 | Wang et al. | |
| 6,770,092 B2 | 8/2004 | Richter | |
| 6,790,224 B2 | 9/2004 | Gerberding | |
| 6,805,697 B1 | 10/2004 | Helm et al. | |
| 6,805,702 B1 | 10/2004 | Chen et al. | |
| 6,824,553 B1 | 11/2004 | Samson et al. | |
| 6,830,575 B2 | 12/2004 | Stenzel et al. | |
| 6,843,802 B1 | 1/2005 | Villalobos et al. | |
| 6,852,116 B2 | 2/2005 | Leonhardt et al. | |
| 6,872,215 B2 | 3/2005 | Crocker et al. | |
| 6,887,268 B2 | 5/2005 | Butaric et al. | |
| 6,911,038 B2 | 6/2005 | Mertens et al. | |
| 6,926,690 B2 | 8/2005 | Renati | |
| 6,986,786 B1 * | 1/2006 | Smith | 623/1.36 |
| 7,481,834 B2 * | 1/2009 | Kaplan et al. | 623/1.15 |
| 7,578,841 B2 | 8/2009 | Yadin et al. | |
| 2001/0008976 A1 | 7/2001 | Wang | |
| 2001/0011188 A1 | 8/2001 | Berry et al. | |
| 2001/0020181 A1 | 9/2001 | Layne | |
| 2001/0023356 A1 | 9/2001 | Raz et al. | |
| 2001/0037137 A1 | 11/2001 | Vardi et al. | |
| 2001/0041930 A1 | 11/2001 | Globerman et al. | |
| 2002/0058984 A1 | 5/2002 | Butaric et al. | |
| 2002/0058993 A1 | 5/2002 | Landau et al. | |
| 2002/0077692 A1 * | 6/2002 | Besselink | 623/1.12 |
| 2002/0111619 A1 | 8/2002 | Keast et al. | |
| 2002/0116047 A1 | 8/2002 | Vardi et al. | |
| 2002/0151959 A1 | 10/2002 | Von Oepen | |
| 2002/0156516 A1 | 10/2002 | Vardi et al. | |
| 2002/0169498 A1 | 11/2002 | Kim et al. | |
| 2002/0173840 A1 | 11/2002 | Brucker et al. | |
| 2002/0183763 A1 | 12/2002 | Callol et al. | |
| 2002/0183780 A1 | 12/2002 | Wang | |
| 2002/0193862 A1 | 12/2002 | Mitelberg et al. | |
| 2002/0193868 A1 | 12/2002 | Mitelberg et al. | |
| 2002/0198559 A1 | 12/2002 | Mistry et al. | |
| 2003/0083734 A1 | 5/2003 | Friedrich et al. | |
| 2003/0097171 A1 | 5/2003 | Elliot | |
| 2003/0114912 A1 | 6/2003 | Sequin et al. | |
| 2003/0125797 A1 | 7/2003 | Chobotov et al. | |
| 2003/0125799 A1 | 7/2003 | Limon | |
| 2003/0199967 A1 | 10/2003 | Hartley et al. | |
| 2004/0015227 A1 | 1/2004 | Vardi et al. | |
| 2004/0024441 A1 | 2/2004 | Bertolino et al. | |
| 2004/0054362 A1 | 3/2004 | Lopath et al. | |
| 2004/0054396 A1 | 3/2004 | Hartley et al. | |
| 2004/0073520 A1 | 4/2004 | Eskandari | |
| 2004/0093058 A1 * | 5/2004 | Cottone et al. | 623/1.11 |
| 2004/0106985 A1 | 6/2004 | Jang | |
| 2004/0133268 A1 | 7/2004 | Davidson et al. | |
| 2004/0138730 A1 | 7/2004 | Mitelberg et al. | |
| 2004/0138737 A1 | 7/2004 | Davidson et al. | |
| 2004/0143209 A1 | 7/2004 | Liu et al. | |
| 2004/0158306 A1 | 8/2004 | Mitelberg et al. | |
| 2004/0204754 A1 | 10/2004 | Kaplan et al. | |
| 2004/0220655 A1 | 11/2004 | Swanson et al. | |
| 2004/0249434 A1 | 12/2004 | Andreas et al. | |
| 2004/0254627 A1 | 12/2004 | Thompson et al. | |
| 2004/0260378 A1 * | 12/2004 | Goshgarian | 623/1.11 |
| 2004/0260383 A1 | 12/2004 | Stelter et al. | |
| 2005/0010278 A1 * | 1/2005 | Vardi et al. | 623/1.15 |
| 2005/0015108 A1 | 1/2005 | Williams et al. | |
| 2005/0049678 A1 | 3/2005 | Cocks et al. | |
| 2005/0154447 A1 | 7/2005 | Goshgarian | |
| 2005/0165469 A1 | 7/2005 | Hogendijk et al. | |
| 2005/0192656 A1 | 9/2005 | Eidenschink | |
| 2005/0203563 A9 | 9/2005 | Pederson, Jr. et al. | |
| 2005/0209674 A1 | 9/2005 | Kutscher et al. | |
| 2005/0228483 A1 | 10/2005 | Kaplan et al. | |
| 2005/0234536 A1 | 10/2005 | Mitelberg et al. | |
| 2005/0251195 A1 | 11/2005 | Wang | |
| 2005/0261722 A1 | 11/2005 | Crocker et al. | |
| 2005/0288769 A1 | 12/2005 | Globerman | |
| 2006/0025849 A1 | 2/2006 | Kaplan et al. | |
| 2006/0116748 A1 | 6/2006 | Kaplan et al. | |
| 2007/0203571 A1 | 8/2007 | Kaplan et al. | |
| 2007/0213803 A1 | 9/2007 | Kaplan et al. | |
| 2007/0213804 A1 | 9/2007 | Kaplan et al. | |
| 2007/0276460 A1 | 11/2007 | Davis et al. | |
| 2008/0015610 A1 | 1/2008 | Kaplan et al. | |
| 2008/0015678 A1 | 1/2008 | Kaplan et al. | |
| 2008/0039919 A1 | 2/2008 | Kaplan et al. | |
| 2008/0183269 A2 | 7/2008 | Kaplan et al. | |
| 2009/0163988 A1 | 6/2009 | Kaplan et al. | |
| 2009/0163999 A1 | 6/2009 | Kaplan et al. | |

FOREIGN PATENT DOCUMENTS

| | | |
|---|---|---|
| EP | 0505686 | 11/1996 |
| EP | 0540290 | 1/1998 |
| EP | 0876805 A2 | 11/1998 |
| EP | 0959811 B1 | 12/1999 |
| EP | 1325715 A2 | 7/2003 |
| EP | 1325716 A1 | 7/2003 |
| EP | 1325717 A2 | 7/2003 |
| EP | 1362564 A1 | 11/2003 |
| EP | 1433441 A2 | 6/2004 |
| EP | 1 512 381 A2 | 3/2005 |
| WO | WO 96/38101 A1 | 12/1996 |
| WO | WO 97/17101 A1 | 5/1997 |
| WO | WO 98/19629 A2 | 5/1998 |
| WO | WO 98/24503 A1 | 6/1998 |
| WO | WO 00/15147 A1 | 3/2000 |
| WO | WO 00/69367 A1 | 11/2000 |
| WO | WO 02/47580 A2 | 6/2002 |
| WO | WO 02/49538 A2 | 6/2002 |
| WO | WO 03/039626 A2 | 5/2003 |
| WO | WO 2004/026180 A2 | 4/2004 |
| WO | WO 2004/058100 A2 | 7/2004 |
| WO | WO 2004/089249 A1 | 10/2004 |
| WO | WO 2004/091428 | 10/2004 |
| WO | WO 2004/103217 A1 | 12/2004 |

OTHER PUBLICATIONS

Chuter, "Endovascular Grafts: History of Minimally Invasive Treatment of Vascular Disease" in: Chuter et al., *Endoluminal Vascular Prosthese*, (Little, Brown & Co., Boston, 1998) pp. 3-17.
Coons, "Self-Expanding Stainless Steel Biliary Stents," *Radiology*, (Mar. 1989) 170 (3 Pt 2):979-983.
Csiro, "A New Team to Fight Arterial Disease," [online] [retrieved on Dec. 16, 2004], Retrieved from: http://wwww.cmit.csiro.au/innovation/19999-12/arterial.htm, 6 pages total.
Lawrence-Brown et al., "The Zenith Endoluminal Stenet-Graft System: Suprarenal Fixation, Safety Features, Modular Components, Fenestration and Custom Crafting" in: Greenhalgh, *Vascular and Endovascular Surgical Techniques*, 4th ed., (London, W.B. Saunders, 2001), p. 219-223.
Resch et al. "The Impact of Stent Design on Proximal Stent-Graft Fixation in th Abdominal Aorta: An Experimental Study", *Eur J Vasc Endovasc Surg.*, (Aug. 2000), 20(2): 190-195.
Song et al., "Esophageal Strictures: Treatment with a New Design of Modified Gianturco Stent," *Radiology* (Sep. 1992), 184:(3):729-734.
U.S. Appl. No. 11/781,201, filed Jul. 20, 2007.
U.S. Appl. No. 11/781,164, filed Jul. 20, 2007.
U.S. Appl. No. 11/744,796, filed May 4, 2007.
U.S. Appl. No. 11/744,812, filed May 4, 2007.

U.S. Appl. No. 11/744,802, filed May 4, 2007.

International Search Report and Written Opinion in PCT Application No. PCT/US04/10591 dated Mar. 11, 2005 in 6 pages.

European Patent Office Communication (first substantive examination report) in Application No. 04 759 166.4-1526 dated Apr. 30, 2007 in 3 pages.

Supplementary European Search Report for Application No. EP 04759166.4 dated Mar. 5, 2007 in 4 pages.

U.S. Appl. No. 10/584,968, filed Jun. 30, 2006.

U.S. Application No. Not Yet Assigned, filed Nov. 21, 2006.

*International Search Report* in PCT Application No. PCT/US05/36987.

International Search Report and Written Opinion in PCT Application No. PCT/US07/85429 dated Jun. 2, 2008 in 10 pages.

U.S. Appl. No. 12/362,300, filed Jan. 29, 2009.

U.S. Appl. No. 12/362,342, filed Jan. 29, 2009.

Serruys, Patrick W et al.; Handbook of Coronary Stents; Jan. 15, 2002; pp. 130-131; Martin Dunitz, Ltd.; London, UK.

Supplemental European Search Report for Application No. EP 05 81 2396 mailed Nov. 18, 2009.

\* cited by examiner

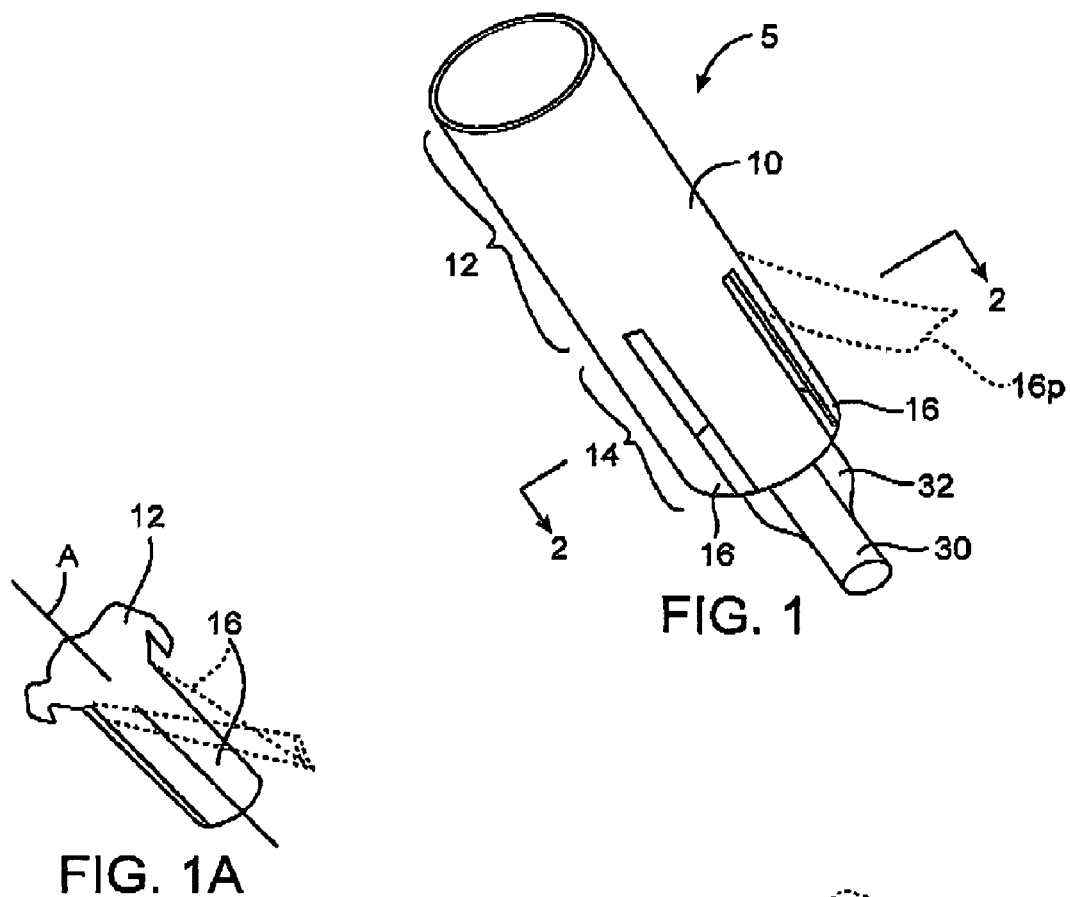
FIG. 1
FIG. 1A
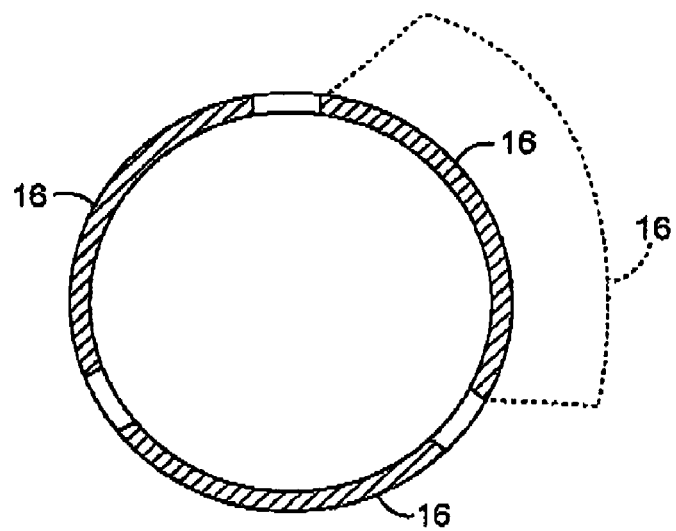
FIG. 2

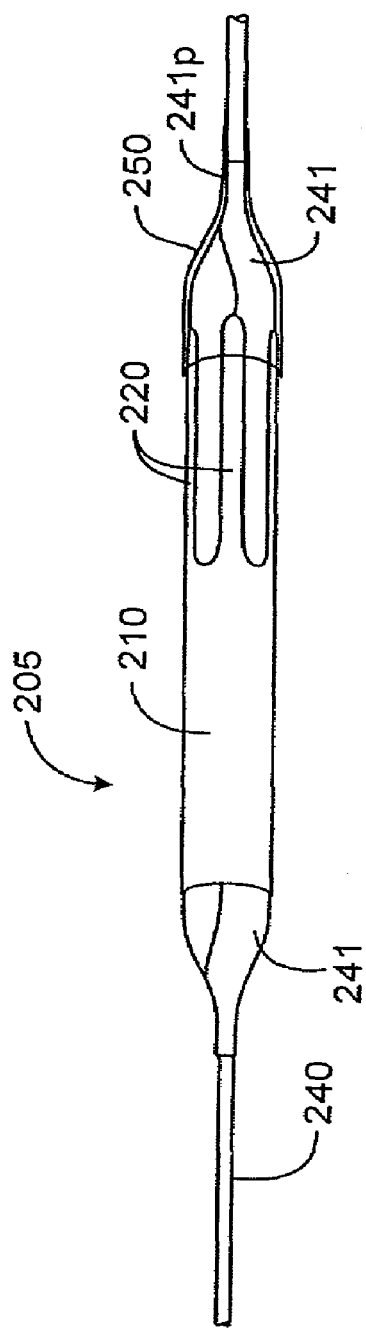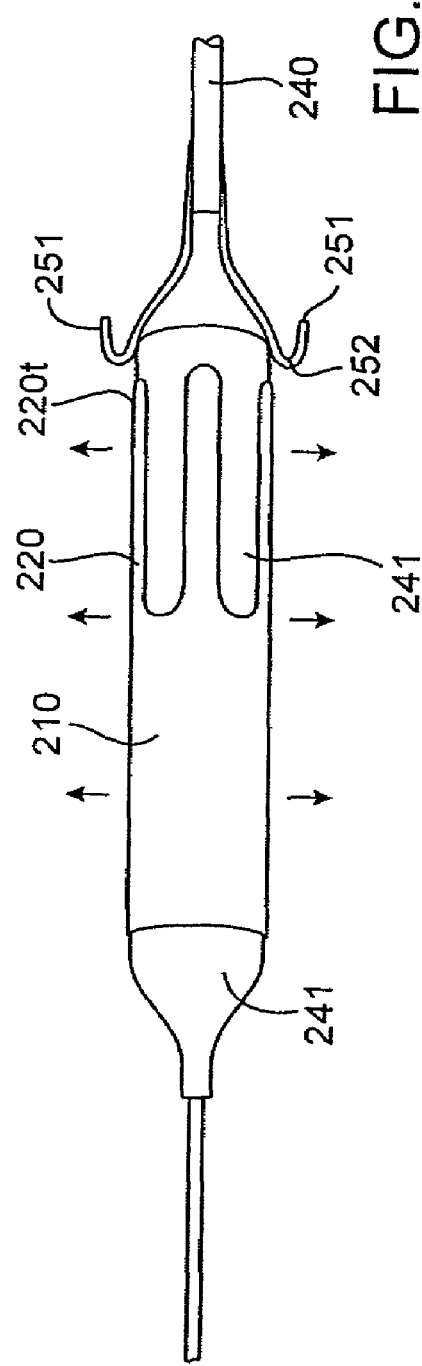
FIG. 6C
FIG. 6D

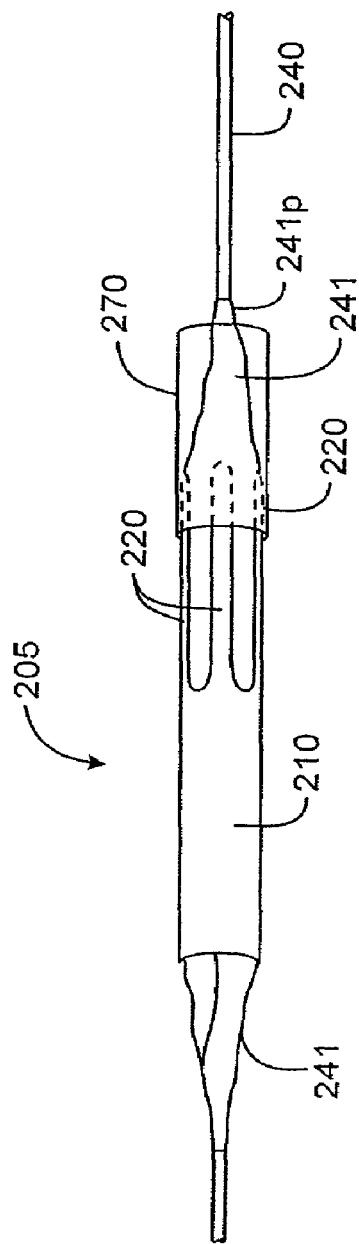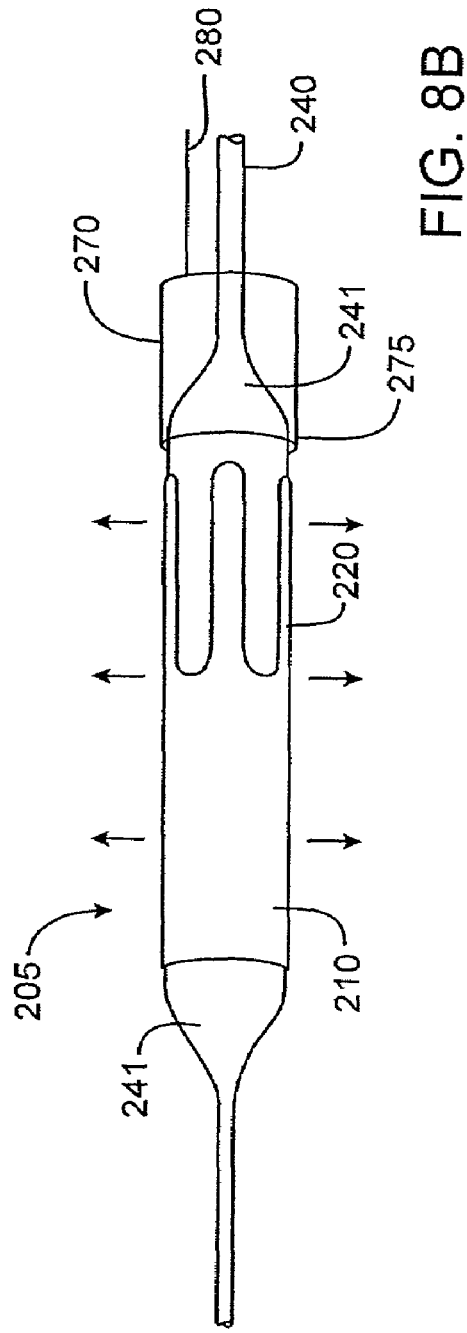

DELIVERY SYSTEM FOR PLACEMENT OF PROSTHESIS AT LUMINAL OS

BACKGROUND OF THE INVENTION

1. Field of the Invention

Embodiments of the present invention relate generally to medical devices and methods. More particularly, embodiments of the present invention relate to the structure and deployment of a segmented stent at a luminal os at a branching point in the vasculature or elsewhere.

Maintaining the patency of body lumens is of interest in the treatment of a variety of diseases. Of particular interest to the present invention are the transluminal approaches to the treatment of body lumens. More particularly, the percutaneous treatment of atherosclerotic disease involving the coronary and peripheral arterial systems. Currently, percutaneous coronary interventions (PCI) often involve a combination of balloon dilation of a coronary stenosis (i.e. a narrowing or blockage of the artery) followed by the placement of an endovascular prosthesis commonly referred to as a stent.

A major limitation of PCI/stent procedures is restenosis, i.e., the re-narrowing of a blockage after successful intervention typically occurring in the initial three to six months post treatment. The recent introduction of drug eluting stents (DES) has dramatically reduced the incidence of restenosis in coronary vascular applications and offers promise in peripheral stents, venous grafts, arterial and prosthetic grafts, as well as A-V fistulae. In addition to vascular applications, stents are being employed in treatment of other body lumens including the gastrointestinal systems (esophagus, large and small intestines, biliary system and pancreatic ducts) and the genital-urinary system (ureter, urethra, fallopian tubes, vas deferens).

Treatment of lesions in and around branch points generally referred to as bifurcated vessels, is a developing area for stent applications, particularly, since 10% of all coronary lesions involve bifurcations. However, while quite successful in treating arterial blockages and other conditions, most stent designs are challenged when used at a bifurcation in the blood vessel or other body lumen. Presently, many different strategies are employed to treat bifurcation lesions with currently available stents all of which have major limitations.

One common approach is to place a conventional stent in the main or larger body lumen over the origin of the side branch. After removal of the stent delivery balloon, a second wire is introduced through a cell in the wall of the deployed stent and into the side branch. A balloon is then introduced into the side branch and inflated to enlarge the side-cell of the main vessel stent. This approach can work well when the side branch is relatively free of disease, although it is associated with increased rates of abrupt closure due to plaque shift as well as increased rates of late re-restenosis.

Another commonly employed strategy is the 'kissing balloon' technique in which separate balloons are positioned in the main and side branch vessels and simultaneously inflated to deliver separate stents simultaneously. This technique is thought to prevent plaque shift.

Other two stent approaches including Culotte, T-Stent and Crush Stent techniques have been employed as well. When employing a T-stent approach, the operator deploys a stent in the side branch followed by placement of a main vessel stent. This approach is limited by anatomic variation (angle between main and side branch) and inaccuracy in stent positioning, which together can cause inadequate stent coverage of the sidebranch os. More recently, the Crush approach has been introduced in which the side-vessel stent is deployed across the os with portions in both the main and side branch vessels. The main vessel stent is then delivered across the origin of the side branch and deployed, which results in crushing a portion of the side branch stent against the wall of the main vessel. Following main-vessel stent deployment, it is difficult and frequently not possible to re-enter the side branch after crush stenting. Unproven long-term results coupled with concern regarding the inability to re-enter the side branch, malaposition of the stents against the arterial wall and the impact of three layers of stent (which may be drug eluting) opposed against the main vessel wall has limited the adoption of this approach.

These limitations have led to the development of stents specifically designed to treat bifurcated lesions. One approach employs a stent design with a side opening for the branch vessel which is mounted on a specialized delivery balloon. The specialized balloon delivery system accommodates wires for both the main and side branch vessels. The system is tracked over both wires which provides a mean to axially and radially align the stent/stent delivery system. The specialized main vessel stent is then deployed and the stent delivery system removed while maintaining wire position in both the main and side branch vessels. The side branch is then addressed using kissing balloon or by delivering and an additional stent to the side branch. Though this approach has many theoretic advantages, it is limited by difficulties in tracking the delivery system over two wires (Vardi et al, U.S. Pat. Nos. 6,325,826 and 6,210,429).

Another approach, of particular interest to the present invention, includes the use of fronds, or fingers extending from the scaffolding of a side branch stent to facilitate positioning of the stent at a bifurcated lesion. This approach is described in detail in co-pending commonly assigned application Ser. No. 10/807,643 the full disclosure of which is incorporated herein.

However while above approach has significant promise, conventional stent delivery systems, such as balloon catheters, can have difficulty managing the fronds during delivery. In such conventional systems, the stent is usually crimped onto the balloon of the balloon catheter. While fine for many conventional stent designs, conventional balloons systems may not always prevent the fronds on a stent from separating from the balloon as the catheter is advanced through curved portions of the vasculature, such as those found in the circumflex coronary artery.

For these reasons, it would be desirable to provide improved systems and methods for delivering stents, particularly stents with fronds or other protruding anchoring elements at one end, to treat body lumens at or near the location of an os between a main body lumen and a side branch lumen, typically in the vasculature, and more particularly in the arterial vasculature. It would be further desirable if such systems and methods could treat the side branch vessels substantially completely in the region of the os and that the prostheses in the side branches be well-anchored at or near the os.

2. Description of the Background Art

Stent structures intended for treating bifurcated lesions are described in U.S. Pat. Nos. 6,599,316; 6,596,020; 6,325,826; and 6,210,429. Other stents and prostheses of interest are described in the following U.S. Pat. Nos. 4,994,071; 5,102, 417; 5,342,387; 5,507,769; 5,575,817; 5,607,444; 5,609,627; 5,613,980; 5,669,924; 5,669,932; 5,720,735; 5,741,325; 5,749,825; 5,755,734; 5,755,735; 5,824,052; 5,827,320; 5,855,598; 5,860,998; 5,868,777; 5,893,887; 5,897,588; 5,906,640; 5,906,641; 5,967,971; 6,017,363; 6,033,434; 6,033,435; 6,048,361; 6,051,020; 6,056,775; 6,090,133; 6,096,073; 6,099,497; 6,099,560; 6,129,738; 6,165,195;

6,221,080; 6,221,098; 6,254,593; 6,258,116; 6,264,682; 6,346,089; 6,361,544; 6,383,213; 6,387,120; 6,409,750; 6,428,567; 6,436,104; 6,436,134; 6,440,165; 6,482,211; 6,508,836; 6,579,312; and 6,582,394.

BRIEF SUMMARY OF THE INVENTION

Embodiments of the present invention provide improved delivery systems for the delivery and placement of stents or other prosthesis within a body lumen, particularly within a bifurcated body lumen and more particularly at an os opening from a main body lumen to a branch body lumen. The delivery systems will be principally useful in the vasculature, most typically the arterial vasculature, including the coronary, carotid and peripheral vasculature; vascular grafts including arterial, venous, and prosthetic grafts, and A-V fistulae. In addition to vascular applications, embodiments of the present invention can also be configured to be used in the treatment of other body lumens including those in the gastrointestinal systems (e.g., esophagus, large and small intestines, biliary system and pancreatic ducts) and the genital-urinary system (e.g., ureter, urethra, fallopian tubes, vas deferens), and the like.

The stent or other prostheses to be delivered will usually comprise a proximal portion which can include anchoring components which can include anchors, fronds, petals or other independently deflectable element extending axially from a main or scaffold section of the stent. These anchoring components can expandably conform to and at least partially circumscribe the wall of the main body vessel to selectively and stably position the prosthesis within the side branch lumen. Further description of exemplary anchoring components and prostheses is found in co-pending application Ser. No. 10/897,643, the full disclosure of which has previously been incorporated herein by reference. Various embodiments of the present invention provide means for capturing or otherwise radially constraining the anchoring components during advancement of the stent through the vasculature (or other body lumen) to a target site and then releasing the anchoring components.

In a first aspect of the invention, a prosthesis delivery system comprises a delivery catheter having an expandable member and a prosthesis carried over the expandable member. The prosthesis has a radially expandable scaffold and at least two fronds extending axially from an end of the scaffold. The system also includes means for capturing the fronds to prevent them from divaricating from the expandable member as the catheter is advanced through a patient's vasculature. Divarication as used herein means the separation or branching of the fronds away from the delivery catheter. Various embodiment of the capture means prevent divarication by constraining and/or imparting sufficient hoop strength to the fronds to prevent them from branching from the expandable member during catheter advancement in the vasculature.

In one embodiment, the capturing means comprises a portion of the expandable member that is folded over the fronds where the folds protrude through axial gaps between adjacent fronds. In another embodiment, the capturing means comprises a cuff that extends over at least a portion of the fronds to hold them during catheter advancement. The cuff can be positioned at the proximal end of the prosthesis and can be removed by expansion of the expandable member to either plastically deform the cuff, break the cuff, or reduce the cuff in length axially as the cuff expands circumferentially. The cuff is then withdrawn from the target vessel. In yet another embodiment, the capturing means can comprise a tether which ties together the fronds. The tether can be configured to be detached from the fronds prior to expansion of the expandable member. In alternative embodiments, the tether can be configured to break or release upon expansion of the expandable member so as to release the fronds.

In an exemplary deployment protocol using the prosthesis delivery system, the delivery catheter is advanced to position the prosthesis at a target location in a body lumen. During advancement, at least a portion of the fronds are radially constrained to prevent divarication of the fronds from the delivery catheter. When the target location is reached, the radial constraint is released and the prosthesis is deployed within the lumen.

In various embodiments, the release of the fronds and expansion of the prosthesis can occur simultaneously or alternatively, the radial constraint can be released prior to expanding/deploying the prosthesis. In embodiments where the radial constraint comprises balloon folds covering the fronds or a cuff or tether, the constraint can be released as the balloon is inflated. In alternative embodiments using a cuff or tether, the cuff/tether can be withdrawn from the fronds prior to expansion of the scaffold.

Embodiments of the above protocol can be used to deploy the prosthesis across the os of a branch body lumen into the main body lumen. In such applications, the prosthesis can be positioned so that the scaffold lies within the branch body and at least two fronds extend into the main body lumen. The fronds are then circumferentially deformed to circumscribe at least a portion of the main vessel wall and open a passage through the fronds. At least three fronds extend into the main body lumen.

Radiopaque or other medical imaging visible markers can be placed on the prostheses and/or delivery balloon at desired locations. In particular, it may be desirable to provide radiopaque markers at or near the location on the prosthesis where the scaffold is joined to the circumferential fronds. Such markers will allow a transition region of the prosthesis between the scaffold and the fronds to be properly located near the os prior to scaffold expansion. The radiopaque or other markers for location the transition region on the prosthesis can also be positioned on a balloon or other delivery catheter. Accordingly, in one embodiment of the deployment protocol, positioning the prosthesis can include aligning a visible marker on at least one of the prosthesis and a delivery balloon with the os.

In various embodiments for deploying the prosthesis, the scaffold is expanded with a balloon catheter expanded within the scaffold. In some instances, the scaffold and the circumferential fronds may be expanded and deformed using the same balloon, e.g., the balloon is first used to expand the anchor, partially withdrawn, and then advanced transversely through the circumferential fronds where it is expanded for a second time. Alternatively, separate balloon catheters may be employed for expanding the scaffold within the side branch and deforming the circumferential fronds within the main body lumen.

By "expandably circumscribe," it is meant that the fronds will extend into the main body lumen after initial placement of the scaffold within the branch body lumen. The circumferential fronds will be adapted to then be partially or fully radially expanded, typically by expansion of a balloon or other expandable element therein, so that the fronds deform outwardly and engage the interior of the main lumen wall.

The circumferential fronds will usually extend axially within the main vessel lumen for some distance after complete deployment. Thus, the contact between the fronds and the main vessel wall will usually extend both circumferentially (typically covering an arc equal to one-half or more of the circumference) and axially.

Expansion of the circumferential fronds at least partially within the main body lumen provides a generally continuous coverage of the os from the side body lumen to the main body lumen. Further and/or complete expansion of the circumferential fronds within the main body lumen may press the fronds firmly against the main body lumen wall and open up the fronds so that they do not obstruct flow through the main body lumen.

Usually, the prosthesis will include at least three circumferential fronds extending axially from the end of the scaffold. The circumferential fronds will have an initial length (i.e., prior to radial expansion of the scaffold) which is at least 1.5 times the width of the scaffold prior to expansion, typically being at least 2 times the width, more typically being at least 5 times the width, and often being 7 times the width or greater. The lengths will typically be at least 2 mm, preferably being at least 3 mm, and more preferably being at least 6 mm, depending on the diameter of the scaffold and prosthesis. The circumferential fronds will usually have a width which is expandable to accommodate the expansion of the scaffold, and the fronds may be "hinged" at their point of connection to the scaffold to permit freedom to adapt to the geometry of the main vessel lumen as the prosthesis is expanded. It is also possible that the fronds could be attached to the single point to the scaffold, thus reducing the need for such expandability. The fronds may be congruent, i.e., have identical geometries and dimensions, or may have different geometries and/or dimensions. In particular, in some instances, it may be desirable to provide fronds having different lengths and/or different widths. Again further description of the fronds may be found in co-pending application Ser. No. 10/807,643.

BRIEF DESCRIPTION OF THE DRAWINGS

FIG. 1 is a schematic illustration of a prosthesis constructed in accordance with the principles of the present invention.

FIG. 1A is a detailed view of an fronds of the prosthesis of FIG. 1, shown with the fronds deployed in broken line.

FIG. 2 is a cross-sectional view taken along line 2-2 of FIG. 1.

FIG. 5A shows pre-deployment, the balloon uninflated; FIG. 5B shows deployment, with the balloon inflated; and FIG. 5C post-deployment, the balloon now deflated.

FIG. 6A shows the balloon in an unexpanded state; and FIG. 6B shows the balloon in an expanded state, with the cuff expanded radially and shrunken axially.

FIGS. 6C-6D are lateral views illustrating an embodiment of a cuff configured to evert upon balloon inflation to release the fronds.

FIGS. 8A-8B are lateral views illustrating an embodiment of a movable sleeve for restraining the stent fronds.

DETAILED DESCRIPTION OF THE INVENTION

Figures 3A, 3B:
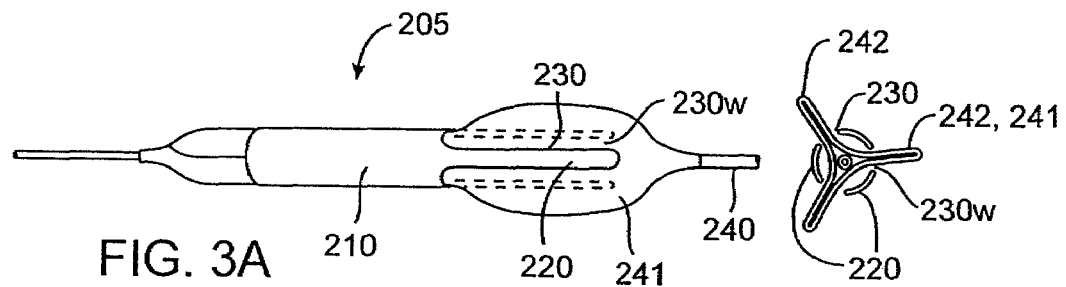
FIGS. 3A and 3B are lateral and cross sectional views illustrating an embodiment of a stent having fronds and an underlying deployment balloon having a fold configuration such that the balloon folds protrude through the spaces between the fronds.
Figures 4A, 4B:
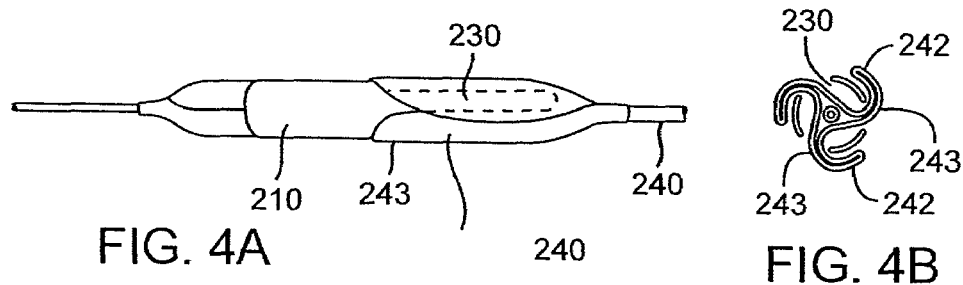
FIGS. 4A and 4B are lateral and cross sectional views illustrating the embodiment of FIGS. 3A and 3B with the balloon folded over to capture the fronds.

Referring now to FIGS. 1 and 2, an embodiment of a delivery system 5 of the present invention for the delivery of a stent to a bifurcated vessel can include a stent or other prosthesis 10 and a delivery catheter 30. Stent 10 can include at least a radially expansible scaffold section 12 and an anchor section 14 with one or more anchors 16 also known as fronds 16. In various embodiments, the anchor section 14 includes at least two axially aligned circumferential fronds 16, with three being illustrated. The radially expansible scaffold section 12 will typically be expandable by an expansion device such as a balloon catheter, but alternatively it can be self expandable. The scaffold section may be formed using a variety of conventional patterns and fabrication techniques as are well-described in the prior art.

Fronds 16, will usually extend axially from the scaffold section 12, as illustrated, but in some circumstances the fronds can be configured to extend helically, spirally, in a serpentine pattern, or other configurations. It is desirable, however, that the individual fronds be radially separable so that they can be independently folded, bent, and otherwise positioned within the main body lumen after the scaffold section 12 has been implanted within the branch body lumen. In the schematic embodiment of FIG. 1, the fronds 16 may be independently folded out in a "petal-like" configuration, forming petals 16p, as generally shown in broken line for one of the fronds in FIGS. 1 and 2.

In preferred embodiments, fronds 16 will be attached to the scaffold section 12 such that they can both bend and rotate relative to an axis A thereof, as shown in broken line in FIG. 1A. Bending can occur radially outwardly and rotation or twisting can occur about the axis A as the fronds are bent outwardly. Such freedom of motion can be provided by single point attachment joints as well as two point attachments or three-point attachments.

Referring now to FIGS. 3A-8, in various embodiments delivery system 5 can include a stent 210 having fronds 220 which are configured to be captured or otherwise radially constrained during advancement of the stent through the vasculature or other body lumen. As shown in FIGS. 3A-3B, fronds 220 can be separated by axial gaps or splits 230 along the length of the stent structure. Splits 230 can have a variety of widths and in various embodiments, can have a width between 0.05 to 2 times the width of the fronds, with specific embodiments of 0.05, 0.25, 0.5, 1 and 2 times the width of the fronds. Fronds 220 can be configured to have sufficient flexibility to be advanced through curved and/or tortuous vessels to reach the more distal portions of the vasculature such as distal portion of the coronary vasculature. This can be achieved through the selection of dimensions and/or material properties (e.g. flexural properties) of the fronds. For example, all or a portion of fronds 220 can comprise a resilient metal (e.g., stainless steel) or a superelastic material known in the art. Examples of suitable superelastic materials include various nickel titanium alloys known in the art such as Nitinol™.

It is desirable to have the fronds captured and held against the delivery catheter or otherwise restrained as the stent is advanced through the vasculature in order to prevent the fronds from divaricating or separating and branching from the scaffold section of the stent. Capture of the fronds and prevention of divarication can be achieved through a variety of means. For example, in various embodiments the capture means can be configured to prevent divarication by imparting sufficient hoop strength to the fronds, or a structure including the fronds, to prevent the fronds from separating and branching from the deployment balloon as the balloon catheter is advanced through the vascular including tortuous vasculature. In theses embodiments, the capture means are also configured to allow the fronds to have sufficient flexibility to be advanced through the vasculature as described above.

In an embodiment shown in FIGS. 3A-4B, the fronds can be captured under the flaps 242 of a deployment balloon 241 of a delivery balloon catheter 240. In this and related embodiments, the balloon 241 and stent 210 can be configured such that flaps 242 are substantially matched up or aligned with splits 230. This can achieved using alignment techniques known in the art (e.g., use of alignment fixtures) when the stent 220 is positioned over balloon 241. The flap material will initially extend or protruded through the splits, but is then folded over onto one or more fronds 220 to capture those fronds. In an embodiment, this can be achieved by partially inflating and then deflating the balloon, with folding done after the inflation or deflation. Folding can be done by hand or using a capture tube or overlying sleeve known in the art. Also in an embodiment, folding can be facilitated by the use of one or more preformed folds 243, also known as fold lines 243. Folds 243 can be formed using medical balloon fabrication methods known in the art such as mold blowing methods known in the art. In an embodiment using folds 243, folding can be achieved by inflating the balloon with the overlying fronds in place, so as to have the balloon flaps 242 protrude through splits 230, then the balloon is a deflated to have flaps 242 fold back over fronds 220 at fold lines 243.

Once stent 210 is properly positioned at the target vessel site, balloon 241 is at least partially inflated which unfurls flaps 242 covering fronds 220 so as to release the fronds. Once released, deployment balloon 241 can also be used to expand or otherwise deform the fronds 220 to deploy them in the selected vessel as is described herein. Alternatively, a second balloon can be to used expand and deploy the fronds as is also described herein.

To avoid pinching the balloon material of balloon 241 between layers of stent metal during the stent crimping process in one embodiment, fronds 220 can be configured such that they do not overlap when crimped down to a smaller diameter. This can be achieved by configuring the fronds to be sufficiently narrow so that crimping the stent to a smaller diameter does not cause them to overlap, or through the use of a crimping fixture or mandrel known in the art. In various embodiments, fronds 220 can be configured to have a selectable minimum split width 230w between splits 230 after crimping. This can be in the range of about 0.001 to about 0.2 inches with specific embodiments of 0.002, 0.005, 0.010, 0.025, 0.050 and 0.1 inches.

In another embodiment for using the delivery balloon catheter to capture the fronds, a section of the balloon 241 (not shown) can be configured to evert or fold back over a proximal portion of the stent and thus overly and capture the fronds. When the balloon is inflated, the overlying section of balloon material unfolds, releasing the fronds. The everted section of balloon can over all or any selected portion of the fronds. Eversion can be facilitated through the use of preformed folds described herein, in this case, the folds having a circumferential configuration. The folded section of balloon can be held in place by a friction fit or through the use of releasable low-strength heat bond or adhesive known in the art for bonding the balloon to the fronds. In one embodiment for positioning the everted section, the balloon is positioned inside the scaffold section of the stent and then partially inflated to have an end of the balloon protrude outside of the scaffold section, then the balloon is partially deflated and the everted section is rolled over the fronds and then the balloon is fully deflated to create a vacuum or shrink fit of the balloon onto the fronds.

Figure 5A:
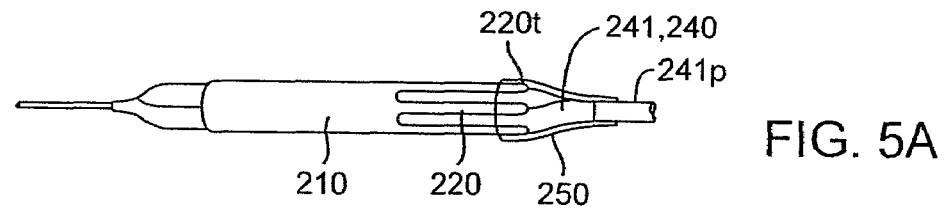
FIGS. 5A-5C are lateral views illustrating the deployment of stent fronds using an underlying deployment balloon and a retaining cuff positioned over the proximal portion of the balloon.
Figure 5B:
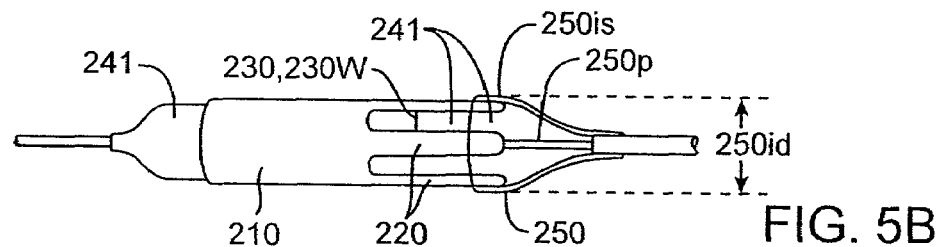
Figure 5C:
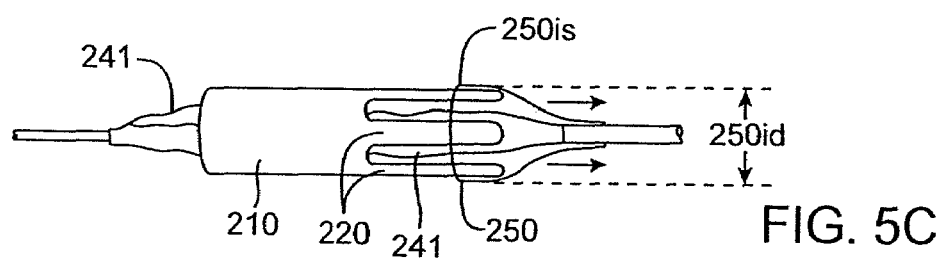

In various embodiments, fronds 210 can also be captured by use of a cuff 250 extending from the proximal end 241p of delivery balloon 241 as is shown in FIGS. 5A-5C. In preferred embodiments the cuff is attached to the catheter at the proximal end 241p of the delivery balloon. In alternative embodiments, the cuff can be attached to a more proximal section of the catheter shaft such that there is an exposed section of catheter shaft between balloon and the cuff attachment point with the attachment point selected to facilitate catheter flexibility. In either approach, the cuff is fixed to the proximal end of the balloon 241p such that it overlies at least a portion of stent fronds 220.

After stent 210 is positioned at the target tissue site, the cuff releases the fronds allowing the stent to be deployed using the delivery balloon as is described herein. After releasing the fronds, the cuff can then be withdrawn prior to or along with the removal of the balloon catheter. In most embodiments, the entire catheter assembly including cuff, balloon, and catheter shaft are withdrawn proximally to fully release the fronds.

Release of the fronds by the cuff can be achieved through a variety of means. In one embodiment, cuff 250 can be configured such the frond tips 220t, slip out from the cuff when the balloon is deployed. Alternatively, the cuff my scored or perforated such that it breaks at least partially open upon balloon deployment so that it releases fronds 220. Accordingly, in such embodiments, cuff 250 can have one or more scored or perforated sections 250p. In such embodiments, portions of cuff 250 can be configured to break open at a selectable inflation pressure or at a selectable expanded diameter.

In various embodiments, cuff 250 can be configured such that it plastically deforms when the balloon is inflated and substantially retains its "inflated shape" 250is and "inflated diameter" 250id after the balloon is deflated is shown in FIGS. 5B and 5C. This can be achieved through the selection of plastically deformable materials for cuff 250 (e.g. plastically deformable polymers), the design of the cuff itself (e.g. cuff dimensions and shape) and combinations thereof. For example, a cuff fixed to the catheter shaft and having the same approximate internal diameter as the deployed stent may be folded over the stent fronds to constrain them (using conventional balloon folding techniques). That cuff may be unfolded when the stent deployment balloon is inflated and the fronds released. The cuff can then be withdrawn along with the balloon and catheter. In an alternative embodiment of a folded-over cuff, the cuff is relatively inelastic and has an internal diameter approximately that of the deployed stent.

Figure 6A:
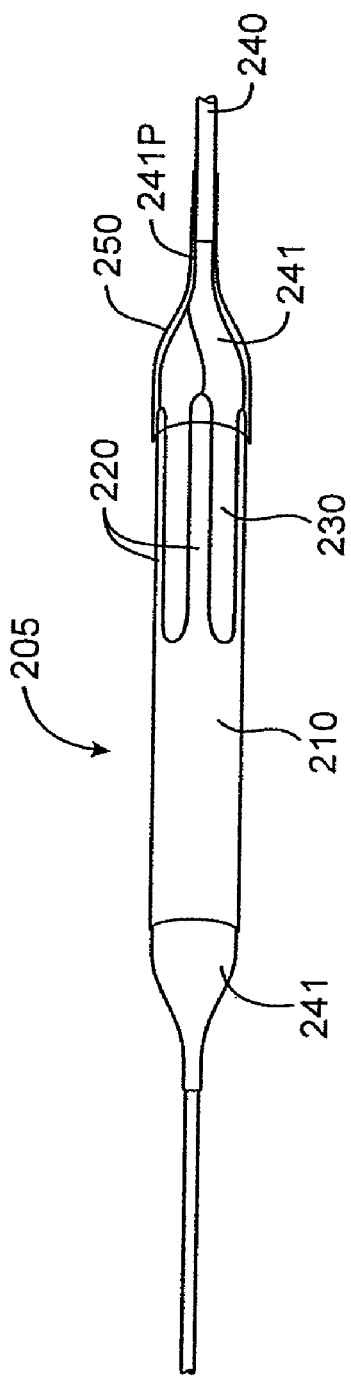
FIGS. 6A-6B are lateral views illustrating the change in shape of the cuff of during deployment of a stent with fronds, of FIG. 6.
Figure 6B:
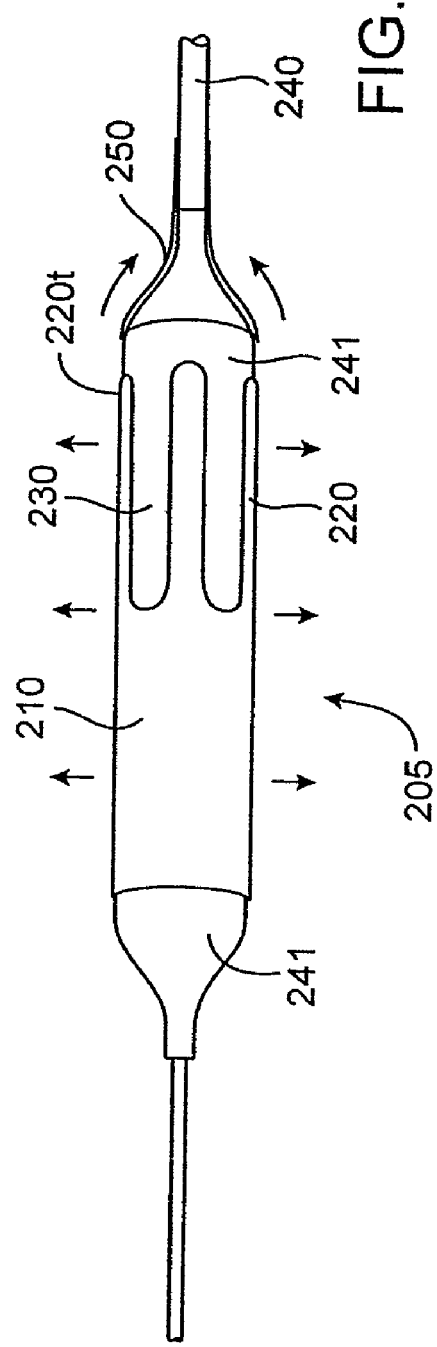

Also the cuff can be configured such that it shortens axially as it is expanded by the deployment balloon or other expansion device. This can be accomplished by selecting the materials for cuff 250 such that cuff shrinks axially when it is stretched radially as is shown in FIGS. 6A and 6B. Accordingly, in one embodiment, the cuff can made of elastomeric material configured to shrink axially when stretched radially.

In another embodiment, all or a portion of the cuff can be configured to fold over or evert onto itself upon inflation of the balloon to produce an everted section 251 and so release the enveloped fronds as is shown in FIGS. 6C-6D. This can be facilitated by use of fold lines 252 described herein, as well as coupling the cuff to the balloon catheter. In one embodiment the cuff can be coaxially disposed over the proximal or distal end of the balloon catheter or even slightly in front of either end. This allows the cuff to disengage the fronds yet remain attached to the balloon catheter for easy removal from the vessel. In use, these and related embodiments allow the fronds to be held against the balloon to be radially constrained or captured during stent advancement and then easily released before, during or after balloon inflation to deploy the stent at the target site.

In various embodiments, all or a portion of cuff 250 can be fabricated from, silicones, polyurethanes (e.g., PEPAX) and other medical elastomers known in the art; polyethylenes; fluoropolymers; polyolefin; as well as other medical polymers known in the art. Cuff 250 can also be made of heat shrink tubing known in the art such as polyolefin or PTFE heat shrink tubing. These materials can be selected to produce a desired amount of plastic deformation for a selected stress (e.g. hoop stress from the inflation of deployment balloon). In particular embodiments, all or a portion of the materials comprising cuff 250 can be selected to have an elastic limit lower than forces exerted by inflation of the deployment balloon (e.g., the force exerted by a 3 mm diameter balloon inflated to 10 atms). Combinations of materials may be employed such that different portions of the cuff (e.g., the proximal and distal sections or the inner and outer surfaces) have differing mechanical properties including, but not limited to, durometer, stiffness and coefficient of friction. For example, in one embodiment the distal portion of the cuff can high a higher durometer or stiffness than a proximal portion of the cuff. This can be achieved by constructing the proximal portion of the cuff from a first material (e.g., a first elastomer) and the distal portion out of a second material (e.g. a second elastomer). Embodiments of the cuff having a stiffer distal portion facilitate maintaining the fronds in a restrained state prior to deployment. In another embodiment, at least a portion of an interior surface of the cuff can include a lubricous material. Examples of suitable lubricious materials include fluoropolymers such as PTFE. In a related embodiment, a portion of the interior of the cuff, e.g., a distal portion, can be lined with a lubricous material such as a fluoropolymer. Use of lubricous materials on the interior of the cuff aids in the fronds sliding out from under the cuff during balloon expansion.

Figure 7A:
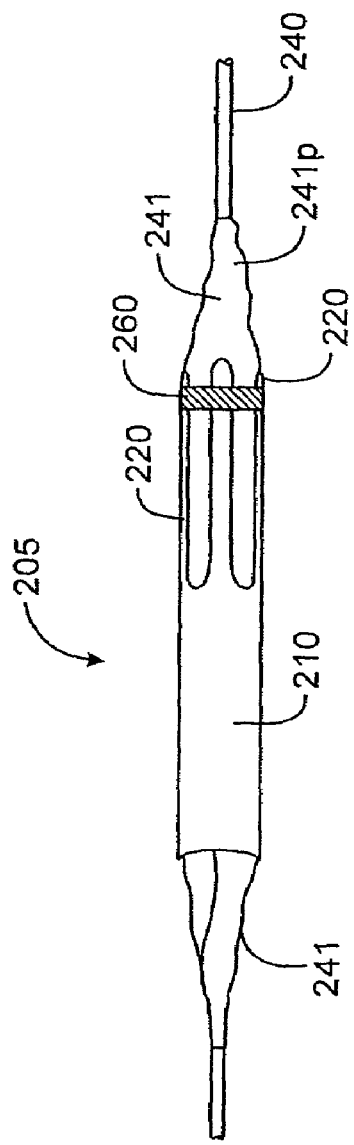
FIGS. 7A-7B are lateral views illustrating an embodiment of a tether for restraining the stent fronds.
Figure 7B:
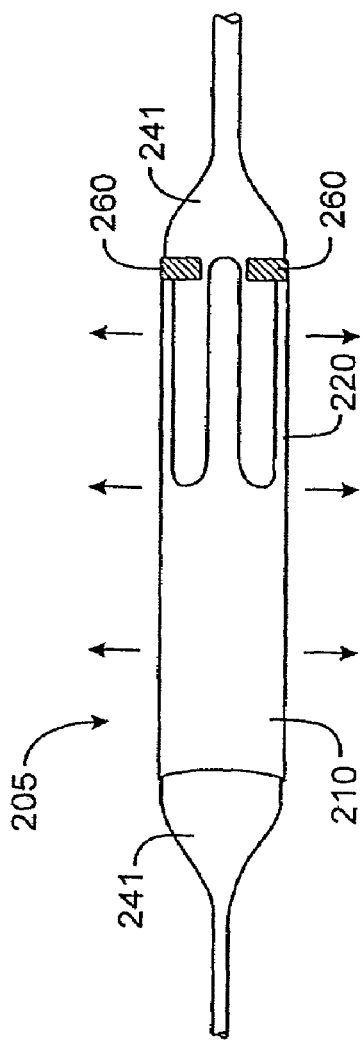

Referring now to FIGS. 7A-7B, in another embodiment for restraining the fronds, a tether 260 can be placed over all or portion of fronds 220 so as to tie the fronds together. Similar to the use of cuff 250, tether 260 can be released by the expansion of the balloon 241. Accordingly, all or a portion of the tether can be configured to plastically deform upon inflation of balloon 241 so as to release the fronds. Alternatively, the tether can be configured to be detached from the fronds prior to expansion of the balloon. In one embodiment, this can be achieved via a pull wire, catheter or other pulling means coupled to the tether directly or indirectly.

In various embodiments, the tether can be a filament, cord, ribbon, etc. which would simply extend around the fronds to capture them like a lasso. In one embodiment the tether can comprise a suture or suture-like material that is wrapped around the fronds. One or both ends of the suture tether can be attachable to the balloon catheter 241. In another embodiment, tether 260 can comprise a band or sleeve that fits over fronds 220 and then expands with expansion of balloon 241.

In this and related embodiments Tether 260 can also be attached to balloon catheter 241. Also, tether 260 can be scored or perforated so that a portion of the tether shears or otherwise breaks upon balloon inflation, thereby releasing the fronds. Further, the tether 260 can contain a radio-opaque other medical image visible marker 260*m* to allow the physician to visualize the position of the tether on the fronds, and/or determine if the tether is constraining the fronds.

Referring now to FIGS. 8A-8B, in other embodiments of the delivery system 10, the fronds can be constrained through the use of a removable sleeve 270 that can be cover all or a portion of fronds 220 during positioning of the stent at the target tissue site and then be removed prior to deployment of the fronds. In one embodiment, sleeve 270 can be slidably advanced and retracted over stent 210 including fronds 220. Accordingly, all or portions of sleeve 270 can be made from lubricous materials such as PTFE or silicone. Sleeve 270 can also include one or more radio-opaque or other imaging markers 275 which can be positioned to allow the physician to determine to what extent the sleeve is covering the fronds. In various embodiments, sleeve 270 can be movably coupled to catheter 240 such that the sleeve slides over either the outer or inner surface (e.g., via an inner lumen) of catheter 240. The sleeve can be moved through the use of a pull wire, hypotube, stiff shaft or other retraction means 280 known in the medical device arts. In one embodiment, sleeve 270 can comprise a guiding catheter or overtube as is known in the medical device arts.

Figure 9A:
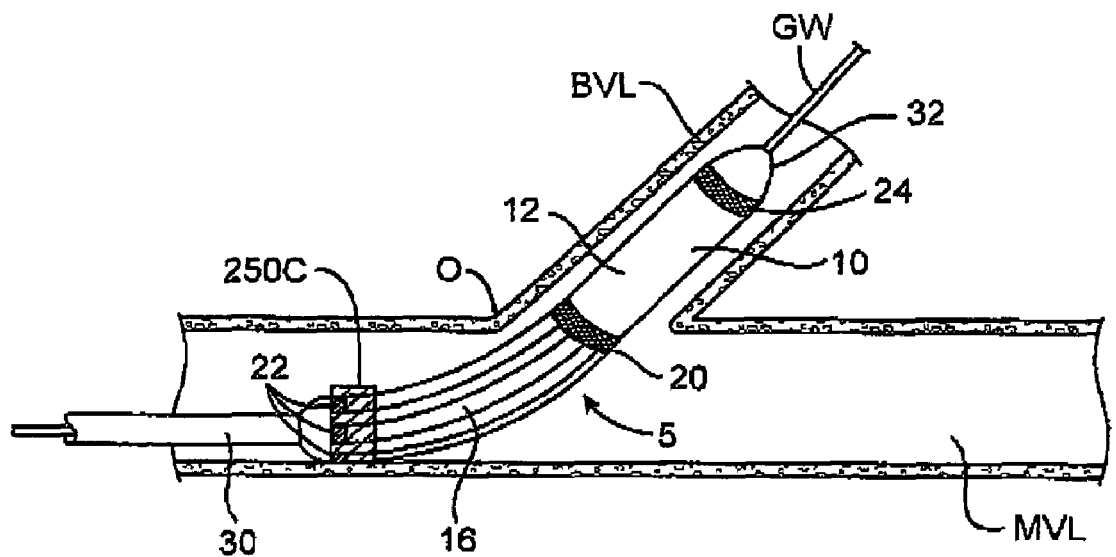
FIGS. 9A-9B, 10A-10B and 11A-11B illustrate deployment of a stent at an os between a main blood vessel and a side branch blood vessel in accordance with the principles of the methods of the present invention.

Referring now to FIGS. 9A-11B, an exemplary deployment protocol for using delivery system 5 to deliver a stent having one or more fronds will be described. The order of acts in this protocol is exemplary and other orders and/or acts may be used. A delivery balloon catheter 30 is advanced within the vasculature to carry stent 10 having fronds 16 to an os O located between a main vessel lumen MVL and a branch vessel lumen BVL in the vasculature, as shown in FIGS. 9A and 9B. Balloon catheter 30 may be introduced over a single guidewire GW which passes from the main vessel lumen MVL through the os O into the branch vessel BVL. Optionally, a second guidewire (not shown) which passes by the os O in the main vessel lumen MVL may also be employed. Usually, the stent 10 will include at least one radiopaque marker 20 on stent 10 located near the transition region between the scaffold section 12 and the circumferential fronds 16. In these embodiments, the radiopaque marker 20 can be aligned with the os O, typically under fluoroscopic imaging.

Figure 10A:
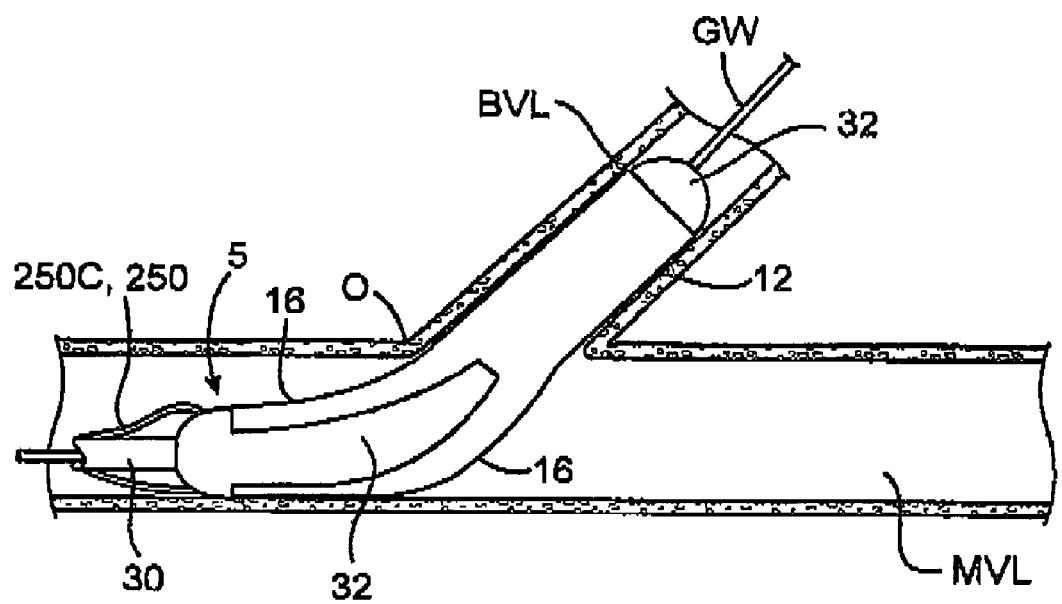
Figure 10B:
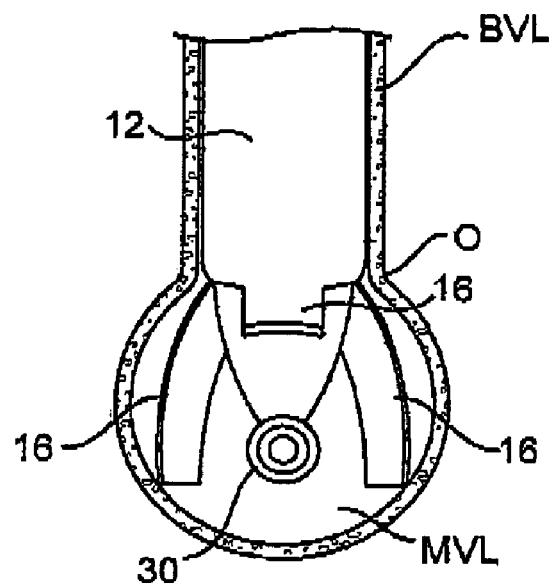

During advancement, the fronds are radially constrained by a constraining means 250*c* described herein (e.g., a cuff or tether) to prevent divarication of the fronds from the delivery catheter. When the target tissue location is reached at os O or other selected location, the constraining means 250*c* is released by the expansion of balloon 32 or other constraint release means described herein (alternatively, the constraining means can be released prior to balloon expansion). Balloon 32 is then further expanded to implant the scaffold region 10 within the branch vessel lumen BVL, as shown in FIGS. 10A and 10B. Expansion of the balloon 32 also partially deploys the fronds 16, opening them in a petal-like manner, as shown in FIG. 10B, typically extending both circumferentially and axially into the main vessel lumen MVL. The fronds 16, however, are not necessarily fully deployed and may remain at least partially within the central region of the main vessel lumen MVL.

Figure 11A:
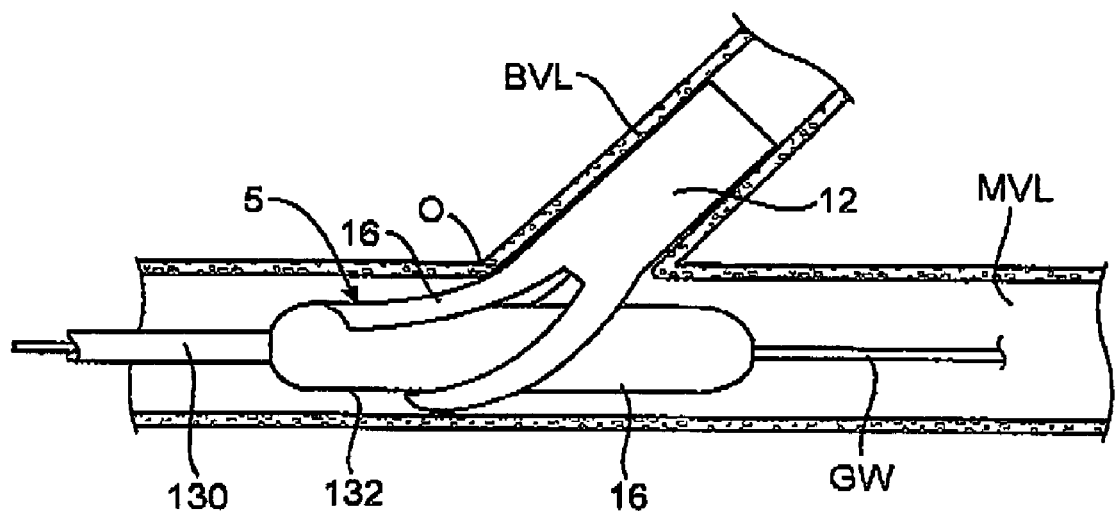
Figure 11B:
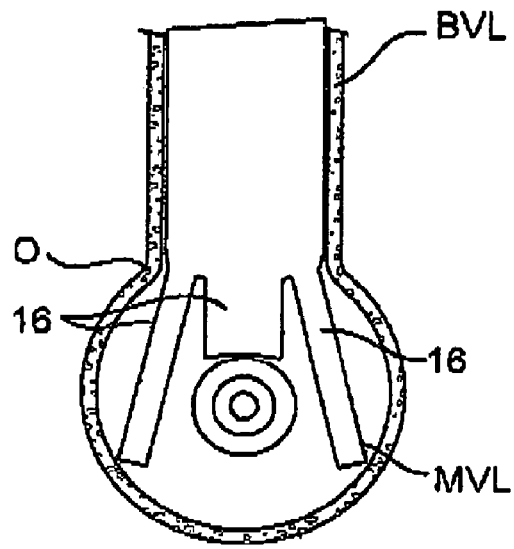

Various approaches can be used in order to fully open the fronds 16. In one embodiment, a second balloon catheter 130 can be introduced over a guidewire GW to position the balloon 132 within the petals, as shown in FIGS. 11A and 11B. Optionally, the first catheter 30 could be re-deployed, for example, by partially withdrawing the catheter, repositioning the guidewire GW, and then advancing the deflated balloon 32 transversely through the fronds 16 and then re-inflating balloon 32 to fully open fronds 16. As it is generally difficult to completely deflate the balloon, however, and a partially inflated balloon would be difficult to pass through the fronds, it will generally be preferable to use a second balloon catheter 130 for fully deforming fronds 16. When using the second balloon catheter 130, a second GW will usually be prepositioned in the main vessel lumen MVL past the os O, as shown in FIGS. 11A and 11B. Further details of various protocols for deploying a stent having fronds or anchors, such as stent 10, are described in co-pending application Ser. No. 10/807,643.

Figure 9B:
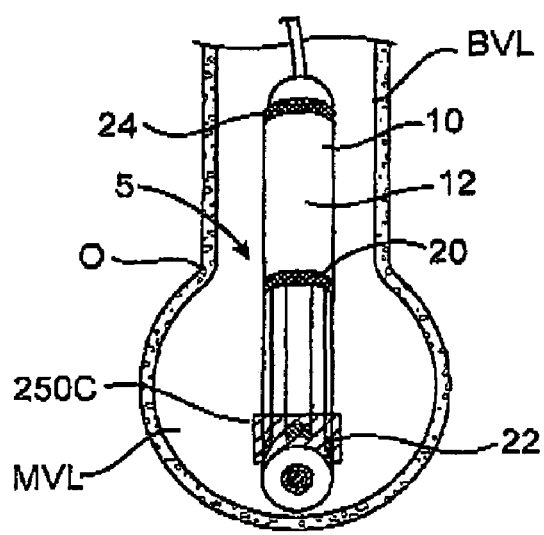

In various embodiments for methods of the invention using delivery system 5, the physician can also make use of additional stent markers 22 and 24 positioned at the ends of stent 10. In one embodiment, one or more markers 22 are positioned at the ends of the fronds as is shown in FIGS. 9A and 9B. In this and related embodiments, the physician can utilize the markers to ascertain the position of the stent as well as the degree of deployment of the fronds (e.g., whether they are in captured, un-captured or deployed state). For example, in one embodiment of the deployment protocol, the physician could ascertain proper positioning of the stent by not only aligning the transition marker 20 with the Os opening O, but also look at the relative position of end markers 22 in main vessel lumen MVL to establish that the fronds are positioned far enough into the main vessel, have not been inadvertently positioned into another branch vessel/lumen and are not hung up on plaque or other vessel blockage. In this way, markers 20 and 22 provide the physician with a more accurate indication of proper stent positioning in a target location in a bifurcated vessel or lumen.

In another embodiment of a deployment protocol utilizing markers 22, the physician could determine the constraint state of the fronds (e.g. capture or un-captured), by looking at the position of the markers relative to balloon 30 and/or the distance between opposing fronds. In this way markers 22 can be used to allow the physician if the fronds were properly released from the constraining means prior to their deployment. In a related embodiment the physician could determine the degree of deployment of the fronds by looking at (e.g., eyeballing) the distance between markers 22 on opposing fronds using one or medical imaging methods known in the art (e.g., X-ray angiography). If one or more fronds are not deployed to their proper extent, the physician could deploy them further by repositioning (if necessary) and re-expanding balloon catheters 30 or 130.

While the above is a complete description of the preferred embodiments of the invention, various alternatives, modifications, and equivalents may be used. Also, elements or steps from one embodiment can be readily recombined with one or more elements or steps from other embodiments. Therefore, the above description should not be taken as limiting the scope of the invention which is defined by the appended claims.

What is claimed is:

1. A method for delivering a luminal prosthesis, said method comprising:
   providing a delivery catheter which carries the prosthesis, wherein the prosthesis comprises a radially expansible scaffold section, at least two anchors each having a distal end coupled with a proximal end of the scaffold section, and at least one opening extending through a side wall of the prosthesis between the at least two anchors and between the scaffold and proximal ends of the anchors, wherein, when expanded, the opening defines a passage;
   advancing the delivery catheter to position the prosthesis at a target location in a body lumen, the target location including an Os opening from a main body lumen to a branch body lumen, wherein at least the anchors are radially constrained by a capturing structure to prevent divarication from the delivery catheter and the scaffold is not radially constrained by a structure that is separable from the delivery catheter;
   positioning the prosthesis so that the scaffold lies within the branch body lumen and all of the anchors extend into the main body lumen;
   expanding the scaffold within the branch body lumen and expanding at least two anchors so that all of the anchors extend into and in a same upstream blood flow direction within the main body lumen when expanded; and
   deploying a second prosthesis within the passage through the at least one opening.

2. A method as in claim 1, further comprising releasing the capturing structure.

3. A method as in claim 2, wherein releasing and expanding occur simultaneously or releasing occurs during expanding.

4. A method as in claim 3, wherein the capturing structure comprises folds of a balloon covering the anchors, wherein the capturing structure is released as the balloon is inflated.

5. A method as in claim 3, wherein the capturing structure comprises a cuff which extends over the anchors.

6. A method as in claim 3, wherein the capturing structure comprises a tether which ties the anchors together, wherein the tether is broken by expansion of the scaffold.

7. A method as in claim 2, wherein the capturing structure is released prior to expanding the scaffold.

8. A method as in claim 7, wherein the capturing structure comprises a cuff which extends over the anchors, wherein the cuff is withdrawn from the anchors prior to expansion of the scaffold.

9. A method as in claim 8, wherein prior to withdrawal, the cuff extends over at least a portion of the scaffold.

10. A method as in claim 7, wherein the capturing structure comprises a tether which ties the anchors together, wherein the tether is withdrawn prior to expansion.

11. A method as in claim 1, wherein expanding the scaffold deforms the anchors to circumscribe at least a portion of the main-body lumen.

12. A method as in claim 11, wherein at least three circumferential anchors extend into the main body lumen.

13. A method as in claim 11, wherein positioning the prosthesis comprises aligning a visible marker on at least one of the prosthesis and a delivery balloon with the os.

14. A method as in claim 11, wherein the lumens are blood vessels.

15. A method as in claim 11, wherein the scaffold is expanded with a balloon expanded within the scaffold.

16. A method as in claim 15, wherein the anchors are deformed by expanding a balloon positioned transversely through the anchors.

17. A method as in claim 16, wherein the scaffold and anchors are expanded and deformed by the same balloon.

18. A method as in claim 16, wherein the scaffold and anchors are expanded and deformed by different balloons.

19. A method as in claim 1, further comprising:
   circumferentially deforming the anchors to circumscribe at least a portion of a wall of the main body lumen and open the passage through the anchors.

20. A method as in claim 1, wherein the second prosthesis is deployed by a balloon catheter exchanged over a guidewire pre-positioned for deformation of the anchors.

21. A method as in claim 1, wherein the anchors are deformed by deployment of the second prosthesis.

22. A method as in claim 1, wherein the deployed second stent supports the anchors over their lengths from the os over the main body lumen wall.

23. The method of claim 1, further comprising circumferentially deforming the anchors such that the anchors circumscribe the main body lumen to reach a wall of the main body lumen opposite the Os opening.

24. A method for delivering a luminal prosthesis, said method comprising:
   providing a delivery catheter which carries the prosthesis, wherein the prosthesis comprises a radially expansible scaffold section and at least two anchors each extending directly from an end thereof;
   advancing the delivery catheter to position the prosthesis at a target location in a body lumen, the target location including an Os opening from a main body lumen to a branch body lumen, wherein at least the anchors are radially constrained by a capturing structure to prevent divarication from the delivery catheter and the scaffold is not radially constrained by a structure that is separable from the delivery catheter;
   positioning the prosthesis so that the scaffold lies within the branch body lumen and the at least two anchors traverse the Os opening and extend into the main body lumen; and
   expanding the scaffold within the branch body lumen and expanding at least two anchors so that all of the anchors extend into and in a same upstream blood flow direction within the main body lumen and the at least two anchors traverse the Os opening when fully deployed.

* * * * *